United States Patent
Bolze et al.

(10) Patent No.: US 12,310,949 B2
(45) Date of Patent: May 27, 2025

(54) USE OF A THIENOPYRIDONE DERIVATIVE IN THE TREATMENT OF AUTOSOMAL DOMINANT POLYCYSTIC KIDNEY DISEASE (ADPKD)

(71) Applicant: POXEL, Lyons (FR)

(72) Inventors: Sébastien Bolze, Massieux (FR); Pascale Fouqueray, Sins (CH); Sophie Hallakou-Bozec, Antony (FR)

(73) Assignee: POXEL, Lyons (FR)

( * ) Notice: Subject to any disclaimer, the term of this patent is extended or adjusted under 35 U.S.C. 154(b) by 0 days.

(21) Appl. No.: 17/915,123

(22) PCT Filed: Apr. 2, 2021

(86) PCT No.: PCT/EP2021/058792
§ 371 (c)(1),
(2) Date: Sep. 28, 2022

(87) PCT Pub. No.: WO2021/198506
PCT Pub. Date: Oct. 7, 2021

(65) Prior Publication Data
US 2023/0120204 A1  Apr. 20, 2023

(30) Foreign Application Priority Data
Apr. 2, 2020 (EP) .................................... 20167687

(51) Int. Cl.
*A61K 31/4365* (2006.01)
*A61P 13/12* (2006.01)

(52) U.S. Cl.
CPC .......... *A61K 31/4365* (2013.01); *A61P 13/12* (2018.01)

(58) Field of Classification Search
None
See application file for complete search history.

(56) References Cited

U.S. PATENT DOCUMENTS

| 9,284,329 | B2* | 3/2016 | Cravo ..................... A61P 43/00 |
| 2022/0017532 | A1 | 1/2022 | Bolze et al. |
| 2023/0112080 | A1 | 4/2023 | Bolze et al. |
| 2023/0149370 | A1 | 5/2023 | Bolze et al. |

FOREIGN PATENT DOCUMENTS

| WO | WO 2014/001554 | 1/2014 |
| WO | WO 2017/011917 | 1/2017 |
| WO | WO 2020/099678 | 5/2020 |

OTHER PUBLICATIONS

Karihaloo A. Role of Inflammation in Polycystic Kidney Disease. In: Li X, editor. Polycystic Kidney Disease [Internet]. Brisbane (AU): Codon Publications; Nov. 2015. Chapter 14. PMID: 27512776. (Year: 2015).*
CAS STNext Registry Database for WO2014001554. Retrieved from the Cas Registry Database Online on Aug. 9, 2023, stn.org (Year: 2023).*
CAS SciFinder PatentPak Database for U.S. Pat. No. 9,284,329. Retrieved from the CAS SciFinder PatentPak Database on Aug. 9, 2023, scifinder-n.cas.org. (Year: 2023).*
Entry from "A Dictionary of Units of Measurement", May 3, 2023, pp. 1-8.
Claims allowed on Jul. 26, 2023 in U.S. Appl. No. 17/914,372 (published as US-2023/0112080), pp. 1-4.
Written Opinion in International Application No. PCT/EP2021/058792, Jun. 9, 2021, pp. 1-9.
Leonhard, W. N. et al. "Salsalate, but not metformin or canagliflozin, slows kidney cyst growth in an adult-onset mouse model of polycystic kidney disease" *EBioMedicine*, Aug. 28, 2019, pp. 436-445, vol. 47.
Anonymous "Poxel—Corporate Presentation", Jan. 1, 2021, pp. 1-57.
Dagorn, P. G. et al. "A novel direct adenosine monophosphate kinase activator ameliorates disease progression in preclinical models of Autosomal Dominant Polycystic Kidney Disease" Kidney International, 2023, pp. 917-929, vol. 103.

* cited by examiner

*Primary Examiner* — James H Alstrum-Acevedo
*Assistant Examiner* — Lauren Wells
(74) *Attorney, Agent, or Firm* — SALIWANCHIK, LLOYD & EISENSCHENK

(57) ABSTRACT

The invention relates to the use of a thienopyridone derivative, or a pharmaceutical composition comprising the same, in the treatment of autosomal dominant polycystic kidney disease (ADPKD).

6 Claims, 2 Drawing Sheets

*: Significantly different compared to control; &: Significantly different compared to metformin 10μM; §: Significantly different compared to metformin 100μM; #: Significantly different compared to metformin 1mM

USE OF A THIENOPYRIDONE DERIVATIVE IN THE TREATMENT OF AUTOSOMAL DOMINANT POLYCYSTIC KIDNEY DISEASE (ADPKD)

CROSS-REFERENCE TO RELATED APPLICATION

This application is the U.S. national stage application of International Patent Application No. PCT/EP2021/058792, filed Apr. 2, 2021.

TECHNICAL FIELD

The invention relates to the use of a thienopyridone derivative in the treatment of autosomal dominant polycystic kidney disease (ADPKD).

TECHNICAL BACKGROUND

Autosomal dominant polycystic kidney disease (ADPKD) is the most common monogenic inherited kidney disease with an incidence of 1 in 500 to 1 in 1000 individuals (P. Igarashi et al., *J. Am. Soc. Nephrol.*, 13(9), 2384-2398, 2002). Mutations in the PKD1 and PKD2 genes coding for polycystin-1 and polycystin-2 are responsible for 85% and 15% of ADPKD cases, respectively. ADPKD is characterized by the progressive development and growth of numerous bilateral renal cysts, resulting in numeral abnormalities, such as acute and chronic pain, kidney stones and urinary tract infections, the most important of which being the loss of renal function. Approximately 70% of patients with ADPKD progress to end-stage renal disease (ESRD) at a median age of 58 years (E. M. Spithoven et al., *Kidney Int.*, 86(6), 1244-1252, 2014).

Numerous therapies for ADPKD have been proposed, targeting various signaling pathways that drive cyst growth. They involve vasopressin receptor inhibitors such as Tolvaptan, somatostatin analogues such as Octreotide and Lanreotide, Pravastatin and tyrosine kinase inhibitors such as Tesevatinib. Among them, Tolvaptan was the first drug treatment approved by the FDA to slow kidney function decline in adults at risk of rapidly progressing ADPKD. However, because of its potential hepatocellular toxicity, Tolvaptan requires frequent monitoring of liver function in patients treated therewith. These compounds target one of the key processes (proliferation or secretion) thought to be involved in the pathogenesis of ADPKD.

Recently, it has been shown that the cystic fibrosis transmembrane conductance regulator (CFTR), which participates in the secretion of cystic fluid and that the mammalian target of rapamycin (mTOR) pathway, which can drive proliferation of cyst epithelial cells, may be both negatively regulated by AMP-activated protein kinase (AMPK). Activators of AMPK could thus target simultaneously the two key processes of ADPKD. In this context, it was suggested to use metformin, a known indirect activator of AMPK, to inhibit both the secretory and proliferative components of cyst expansion and thus slow renal cystogenesis (V. Takiar et al., *PNAS*, Vol. 108, No. 6, 2462-2467, 2011). However, metformin is known to induce lactic acidosis as a side effect. Since metformin is cleared by the kidney, chronical renal disease has been considered a potential predisposing factor for this complication. In addition, there are concerns that therapeutic AMPK activation with metformin in human kidney may require a high oral dose thereof, at least because of its reduced bioavailability.

It has been suggested that, besides metformin, other AMPK activators could be useful in the treatment of ADPKD. WO2017/011917 thus discloses a number of thienopyridones defined by broad formulae, with no indication as to how they can be synthetized and which specific compounds are included.

More recently, salsalate, a prodrug dimer of salicylate and a direct AMPK activator, was shown to be more effective in reducing cystic kidney disease severity in mutant mice than metformin (W. N. Leohnard et al., *EBioMedicine*, Vol. 47, 436-445, 2019). Salsalate activates AMPK through direct interactions with the drug binding domain of the AMPK 31 isoform. However, the oral dose of salsalate required for providing a therapeutic effect remains high, despite its better bioavailability compared to metformin.

Hence, there remains the need for alternative compounds that would be useful in the treatment of ADPKD at lower doses and/or with greater efficacy and/or with reduced side effects compared to the compounds proposed for this purpose.

The inventors have now shown that specific thienopyridone derivatives could be used in the treatment of ADPKD with lower oral doses than other AMPK activators. These compounds were broadly disclosed as AMPK activators in WO 2014/001554 but it has never been suggested so far to use them in the treatment of ADPKD. They have proven to be direct activators of various AMPK isoforms, including the 31 subunit.

SUMMARY OF THE INVENTION

This invention relates to a thienopyridone derivative of Formula (I):

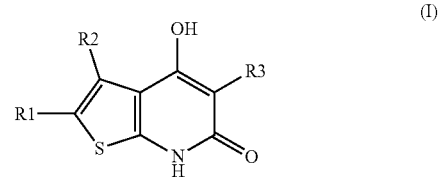

wherein:
R1 represents a hydrogen atom or a halogen atom,
R2 represents an indanyl or tetralinyl group, substituted or not by one or more (e.g. 2, 3, 4, 5, 6 or 7) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups,
R3 represents an aryl group, substituted or not by one or more (e.g. 2, 3, 4 or 5) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups, or its pharmaceutically acceptable salts and/or solvates, or a pharmaceutical composition comprising the same, for use in the treatment of ADPKD.

The present invention also relates to a method for the treatment of ADPKD, comprising administering to a subject in need thereof an effective amount of a thienopyridone derivative as described above, or a pharmaceutical composition comprising an effective amount of a thienopyridone derivative as described above and a pharmaceutically acceptable support.

The present invention also relates to the use of a thienopyridone derivative as described above, or a pharmaceutical composition comprising the same, for the manufacture of a medicament for the treatment of ADPKD.

DETAILED DESCRIPTION OF THE INVENTION

Definitions

Figure 1:
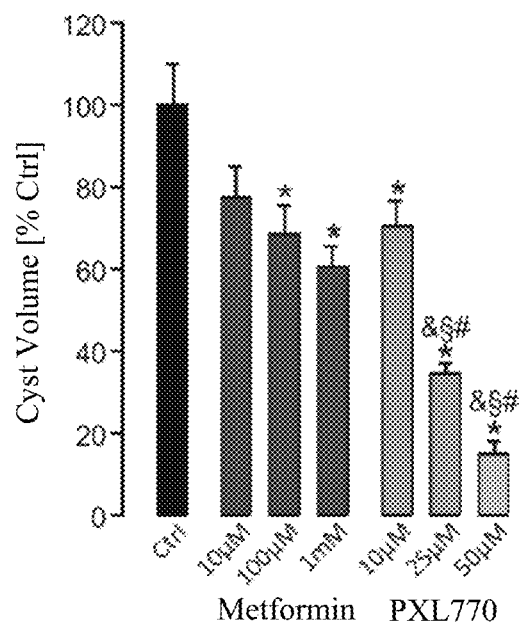
FIG. 1 shows the volume of cysts formed from pIMDCK cells in the presence of 10 µM, 100 µM and 1 mM metformin or of 10 µM, 25 µM or 50 µM PXL770, compared to control medium.

As used herein, the following terms are defined with the following meanings unless explicitly stated otherwise.

The term "halogen atom" refers to an atom selected from fluorine, chlorine, bromine and iodine atoms.

The term "alkyl group" refers to a linear or branched saturated chain of 1 to 5 carbon atoms, such as methyl, ethyl, n-propyl, iso-propyl, n-butyl, sec-butyl, iso-butyl or tert-butyl.

Preferably, alkyl groups are linear or branched saturated chains of 1 to 3 carbon atoms, such as methyl, ethyl, n-propyl or iso-propyl groups.

The term "aryl group" refers to a C6-C18 aromatic group, such as phenyl or naphthyl group, optionally substituted by one or more atoms or groups selected from halogen atoms, alkyl groups, hydroxy (OH), alkyloxy groups, amino ($NH_2$), mono- or di-alkylamino groups, carboxy (COOH), alkyloxycarbonyl groups, mono- or di-alkylaminocarbonyl groups, carboxamide ($CONH_2$), cyano (CN), alkylsulfonyl groups and trifluoromethyl ($CF_3$). More specifically, the aryl group can be substituted or not by fluorine, chlorine, bromine atoms, hydroxy, methoxy, ethoxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methylsulfonyl, or trifluoromethyl group.

The term "aralkyl group" refers to alkyl group as defined above, a hydrogen atom of which is replaced by an aryl group as defined above. An example of an aralkyl group is a benzyl group.

The term "alkyloxy" (or "alkoxy") group refers to an alkyl group as defined above linked to the rest of the molecule through an oxygen atom. Among alkyloxy groups mention can be made of methoxy and ethoxy groups.

The term "aralkyloxy" group refers to an aralkyl group as defined above linked to the rest of the molecule through an oxygen atom. Among aralkyloxy groups mention can be made of the benzyloxy group.

The term "alkylamino group" refers to an alkyl group as defined above linked to the rest of the molecule through a nitrogen atom. Among alkylamino groups mention can be made of dimethylamino and diethylamino groups.

The term "alkyloxycarbonyl group" refers to an alkyloxy group as defined above linked to the rest of the molecule through a carbonyl group.

The term "alkylaminocarbonyl group" refers to an alkylamino group as defined above linked to the rest of the molecule through a carbonyl group.

The term "alkylsulfonyl" refers to an alkyl as defined above linked to the rest of the molecule through a $SO_2$ group. Among alkylsulfonyl groups mention can be made of methylsulfonyl and ethylsulfonyl groups.

"Solvates" of the compounds are taken in the present invention to mean adductions of inert solvent molecules onto the compounds which form owing to their mutual attractive force. Solvates are, for example, hydrates or alcoholates.

This invention pertains to thienopyridone derivatives of Formula (I):

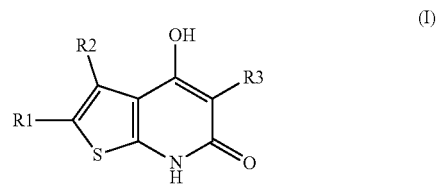

wherein:
R1 represents a hydrogen atom or a halogen atom,
R2 represents an indanyl or tetralinyl group, substituted or not by one or more (e.g. 2, 3, 4, 5, 6 or 7) groups selected from halogen atoms, alkyl groups, hydroxy, alkoxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups,
R3 represents an aryl group, substituted or not by one or more (e.g. 2, 3, 4 or 5) atoms or groups selected from halogen atoms, alkyl groups, hydroxy, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups, or their pharmaceutically acceptable salts and/or solvates, or a pharmaceutical composition comprising the same, for use in the treatment of ADPKD.

Examples of pharmaceutically acceptable salts of the compound of formula (I) can be obtained by reacting the compound of formula (I) with various organic and inorganic bases by procedures usually known in the art to give the corresponding base-addition salt. Such bases are, for example, alkali metal hydroxides, including potassium hydroxide, sodium hydroxide and lithium hydroxide; alkali metal carbonates, including potassium carbonate and sodium carbonate; alkaline earth metal hydroxides, such as barium hydroxide and calcium hydroxide; alkaline earth metal carbonates; alkali metal alkoxides, for example potassium ethoxide and sodium propoxide; and various organic bases, such as piperidine, diethanolamine and N-methylglutamine. The aluminium salts of the compounds of formula (I) are likewise included.

The salts of the compound of formula (I) thus include aluminium, ammonium, calcium, copper, iron(III), iron(II), lithium, magnesium, manganese(II), manganese(II), potassium, sodium and zinc salts, but this is not intended to represent a restriction. Of the above-mentioned salts, preference is given to the mono-, di- and tri-sodium or potassium salts and most preferably to the potassium salts.

Any of the pharmaceutically acceptable salts of the compound of formula (I), or this compound itself, may be used in this invention in the form of one of its solvates. "Solvates" of the compounds are taken in the present invention to mean adductions of inert solvent molecules onto the compounds which form owing to their mutual attractive force. The nature of the solvate thus depends on the solvent used during the reaction of the base with the compound of formula (I). Examples of solvates include alcohol solvates, for instance methanol or ethanol solvates, and hydrates, including mono-, di-, tri- or tetrahydrates, but this is not intended to represent a restriction.

In a particular embodiment, at least one of the following conditions is met and preferably all of them:
R1 represents a halogen atom, in particular a chlorine atom,
R2 is unsubstituted or substituted by 1 or 2 substituents including at least one hydroxy group,
R2 is a tetralinyl group,
R3 represents a phenyl group, which is unsubstituted or substituted by 1 or 2 substituents,
the compound of formula (I) is in the form of a salt, preferably a sodium or potassium salt, more preferably a potassium salt,
the compound of formula (I) is in the form of a solvate, preferably a hydrate, more preferably a monohydrate.

Still preferably, at least one of the following conditions is met and preferably all of them:
R1 represents a halogen atom, in particular a chlorine atom,
R2 is substituted by 1 or 2 substituents including at least one hydroxy group,
R2 is a tetralinyl group,
R3 represents a phenyl group, which is unsubstituted,
the compound of formula (I) is in the form of a salt, preferably a sodium or potassium salt, more preferably a potassium salt,
the compound of formula (I) is in the form of a solvate, preferably a hydrate, more preferably a monohydrate.

In another embodiment, at least one of the following conditions is met and preferably all of them:
R1 represents a halogen atom, in particular a chlorine atom,
R2 is substituted by 1 or 2 substituents including at least one hydroxy group,
R2 is an indanyl group,
R3 represents a phenyl group, which is unsubstituted or substituted by 1 or 2 substituents.

Examples of thienopyridone derivatives according to this invention are the following:
2-chloro-4-hydroxy-3-indan-5-yl-5-phenyl-7H-thieno[2,3-b]pyridin-6-one
2-chloro-5-(4-fluorophenyl)-4-hydroxy-3-indan-5-yl-7H-thieno[2,3-b]pyridin-6-one
2-chloro-4-hydroxy-3-indan-5-yl-5-(3-methoxyphenyl)-7H-thieno[2,3-b]pyridin-6-one
2-chloro-4-hydroxy-3-indan-5-yl-5-(4-methoxyphenyl)-7H-thieno[2,3-b]pyridin-6-one
3-(2-chloro-4-hydroxy-3-indan-5-yl-6-oxo-7H-thieno[2,3-b]pyridin-5-yl)benzonitrile
2-chloro-4-hydroxy-3-indan-5-yl-5-(3-methylphenyl)-7H-thieno[2,3-b]pyridin-6-one
2-chloro-5-(4-fluorophenyl)-4-hydroxy-3-(4-hydroxyindan-5-yl)-7H-thieno[2,3-b]pyridin-6-one
2-chloro-5-(3-fluorophenyl)-4-hydroxy-3-(4-hydroxyindan-5-yl)-7H-thieno[2,3-b]pyridin-6-one
2-chloro-4-hydroxy-3-(4-hydroxyindan-5-yl)-5-phenyl-7H-thieno[2,3-b]pyridin-6-one
2-chloro-5-(2-fluorophenyl)-4-hydroxy-3-(4-hydroxyindan-5-yl)-7H-thieno[2,3-b]pyridin-6-one
2-chloro-4-hydroxy-3-(5-hydroxytetralin-6-yl)-5-phenyl-7H-thieno[2,3-b]pyridin-6-one
3-(2-chloro-4-hydroxy-6-oxo-3-tetralin-6-yl-7H-thieno[2,3-b]pyridin-5-yl)benzonitrile
Trisodium 2-chloro-3-(5-oxidotetralin-6-yl)-5-phenyl-thieno[2,3-b]pyridine-4,6-diolate
2-chloro-4-hydroxy-5-phenyl-3-tetralin-6-yl-7H-thieno[2,3-b]pyridin-6-one
2-chloro-5-(4-fluorophenyl)-4-hydroxy-3-(5-hydroxytetralin-6-yl)-7H-thieno[2,3-b]pyridin-6-one
disodium 2-chloro-3-(5-oxidotetralin-6-yl)-6-oxo-5-phenyl-7H-thieno[2,3-b]pyridin-4-olate
2-chloro-4-hydroxy-3-(5-hydroxytetralin-6-yl)-5-(3-methylphenyl)-7H-thieno[2,3-b]pyridin-6-one
2-chloro-4-hydroxy-3-(5-hydroxytetralin-6-yl)-5-(4-methylphenyl)-7H-thieno[2,3-b]pyridin-6-one
2-chloro-5-(3-fluorophenyl)-4-hydroxy-3-(5-hydroxytetralin-6-yl)-7H-thieno[2,3-b]pyridin-6-one
sodium 2-chloro-3-(5-hydroxytetralin-6-yl)-6-oxo-5-phenyl-7H-thieno[2,3-b]pyridin-4-olate
potassium 2-chloro-3-(5-hydroxytetralin-6-yl)-6-oxo-5-phenyl-7H-thieno[2,3-b]pyridin-4-olate.

The compounds of formula (I) may generally be prepared as disclosed in WO 2014/001554.

Examples of such compounds include:
PXL770 which is the monohydrate potassium salt of 2-chloro-4-hydroxy-3-(5-hydroxytetralin-6-yl)-5-phenyl-7H-thieno[2,3-b]pyridin-6-one corresponding to the following structure of formula (Ia):

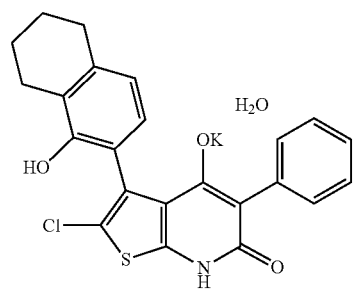

(Ia)

2-chloro-5-(3-fluorophenyl)-4-hydroxy-3-(4-hydroxyindan-5-yl)-7H-thieno[2,3-b]pyridin-6-one having Formula (Ib):

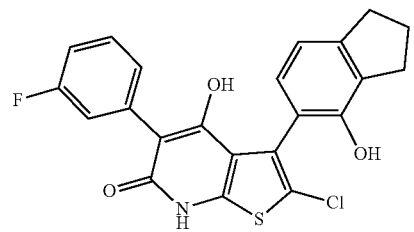

(Ib)

2-chloro-4-hydroxy-3(4-hydroxyindan-5-yl)-5-phenyl-7H-thieno[2,3-b)]pyridin-6-one having Formula (Ic):

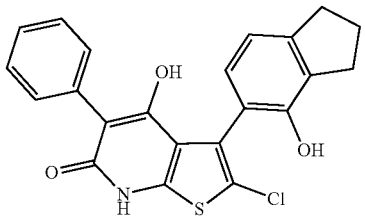

(Ic)

PXL770 may be prepared according to a process comprising the steps of:
(A) reacting a compound of formula (II) with potassium carbonate in a solution comprising water and a solvent selected from n-butyl acetate and isopropanol:

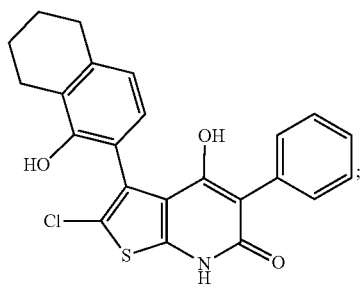

(II)

(B) forming a precipitate; and
(C) recovering the precipitate obtained in step (B), preferably by filtration.

The compound of formula (II) and a preparation process thereof have been disclosed in patent application WO 2014/001554.

Alternatively, said compound of formula (II) may be obtained by an improved process comprising the steps of:
(a) reacting 6-acetyl-5-hydroxytetralin with an electrophilic benzyl source, preferably benzyl bromide, in the presence of a base;
(b) reacting the compound obtained in step (a) with ethyl cyanoacetate in the presence of hexamethyldisilazane and acetic acid;
(c) reacting the compound obtained in step (b) with sulfur in the presence of a base;
(d) optionally forming a salt of the compound obtained in step (c), preferably a hydrochloride salt;
(e) reacting the compound obtained in step (c) or (d) with an electrophilic chlorine source, preferably N-chlorosuccinimide;
(f) reacting the compound obtained in step (e) with phenylacetyl chloride;
(g) reacting the compound obtained in step (f) with a base;
(h) reacting the compound obtained in step (g) with boron tribromide or trichloride, preferably boron trichloride; and
(i) optionally recovering the compound obtained in step (h).

Typically, step (B) can comprise a substep (b1) of heating the mixture obtained in step (A), preferably at a temperature close to reflux of the mixture, followed by a substep (b2) of cooling the resulting mixture, for instance at a temperature comprised between −15° C. and 35° C. The expression "close to reflux of the mixture" refers typically to a temperature comprised between 90% and 100% of the boiling point of the solvent system in step (A) (for instance, water/isopropanol or water/n-butyl acetate).

A distillation step, preferably under reduced pressure, can be carried out between the heating substep and substep (b2).

Step (B) allows a crystalline precipitate to form, which formation may be favored or triggered by adding seeds to steps (b2).

In a preferred embodiment, said precipitate is recovered by filtration in step (C). It may then be washed successively with one or more solvents, preferably water, n-butyl acetate and/or tert-butyl methyl ether.

The compound of formula (Ia), i.e. PXL770, is thus obtained in the form of a solid, such as a powder, having the following XRPD (X-Ray Powder Diffraction) peaks, as measured by means of a diffractometer, using Cu K(alpha) radiation:

| 2-theta (°) | d-value (Å) |
|---|---|
| 13.010 | 6.7992 |
| 14.720 | 6.0130 |
| 17.330 | 5.1128 |
| 19.640 | 4.5164 |
| 21.170 | 4.1933 |
| 22.700 | 3.9140 |
| 23.860 | 3.7263 |
| 24.410 | 3.6435 |
| 26.730 | 3.3323 |
| 28.700 | 3.1079 |
| 30.960 | 2.8860 |
| 34.750 | 2.5794 |
| 35.530 | 2.5246 |
| 35.950 | 2.4960 |
| 36.660 | 2.4493 |

In the following description, the wording "the thienopyridone derivative" refers to the compound of formula (I) or to one of its pharmaceutically acceptable salts and/or solvates.

An object of the present invention is a method for treating autosomal dominant polycystic kidney disease (ADPKD), the method comprising administering to a subject in need thereof an effective amount of the thienopyridone derivative or a pharmaceutical composition comprising an effective amount of the thienopyridone derivative and a pharmaceutically acceptable support.

The invention furthermore relates to the use of the thienopyridone derivative, or a composition comprising the same, in the manufacture of a medicament for the treatment of autosomal dominant polycystic kidney disease (ADPKD).

The pharmaceutical composition used according to the invention may be prepared by any conventional method. The thienopyridone derivative can be converted into a suitable dosage form together with at least one solid, liquid and/or semi-liquid excipient or adjuvant and, if desired, in combination with one or more further active ingredients.

The term "pharmaceutically acceptable support" refers to carrier, adjuvant, or excipient acceptable to the subject from a pharmacological/toxicological point of view and to the manufacturing pharmaceutical chemist from a physical/chemical point of view regarding to composition, formulation, stability, subject acceptance and bioavailability.

The term "carrier", "adjuvant", or "excipient" refers to any substance, not itself a therapeutic agent, that is added to a pharmaceutical composition to be used as a carrier, adjuvant, and/or diluent for the delivery of a therapeutic agent to a subject in order to improve its handling or storage properties or to enable or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc.

The terms "treatment", "treating" and "treat" refer to therapy, prevention and prophylaxis of autosomal dominant polycystic kidney disease (ADPKD). As disclosed herein, the term "treatment" or "treating" refers to the prophylaxis of a disease or at least one of its symptoms. This also means an improvement, prevention of at least one measurable physical parameter associated with the disease being treated, which is discernible or not in the subject. The term "treatment" or "treating" further refers to inhibiting or slowing the progression of the disease, physically, stabilization of a discernible symptom, physiologically, for example, stabilization of a physical parameter, or both. The term "treatment" or "treating" also refers to delaying the onset of a disease or disorder. In some particular embodiments, the compound of the invention is administered as a preventive measure. In this context, "prevention" or "preventing" refers to a reduction in the risk of developing at least one of the symptoms related to the disease.

The term "treating" can include preventing or limiting cyst growth with the thienopyridone derivative or a pharmaceutical composition comprising the same. "Treatment," as used herein, also covers reducing cyst volume. Thus, the terms "treat", "treating," "treatment," and the like, include the treatment of symptoms related to ADPKD.

The treatment involves the administration of the thienopyridone derivative or a pharmaceutical composition of the invention to a subject having a declared disorder to cure, delay, or slow down the progress, thus improving the condition of patients.

Within the context of the invention, the term "subject" means a mammal and more particularly a human. The subjects to be treated according to the invention can be appropriately selected on the basis of several criteria associated to the disease. In the case of ADPKD, the treatment is more particularly suitable for a patient having at least one mutation in the PKD1 and/or PKD2 gene or for a patient at risk of ADPKD. A patient "at risk of ADPKD" encompasses patients aged 15-39 years old with three or more unilateral or bilateral renal cysts, patients aged 40-59 years old with two or more cysts in each kidney and patients aged 60 years old or more with four or more cysts in each kidney, as detected by ultrasonography. Alternatively, patients of 30 years old or younger with at least ten renal cysts, as observed by magnetic resonance imaging, are usually considered at risk of ADPKD.

Pharmaceutical compositions can be administered in the form of dosage units which comprise a predetermined effective amount of active ingredient per dosage unit.

Pharmaceutical compositions can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such compositions can be prepared using all processes known in the pharmaceutical art by, for example, combining the active ingredient with the excipient(s) or adjuvant(s). Preferably, the pharmaceutical composition according to the invention is adapted for oral administration.

Pharmaceutical compositions adapted for oral administration can be administered as separate units, such as, for example, capsules or tablets; powders or granules; solutions or suspensions in aqueous or non-aqueous liquids; edible foams or foam foods; or emulsions, such as oil-in-water liquid emulsions or water-in-oil liquid emulsions.

Thus, for example, in the case of oral administration in the form of a tablet or capsule, the active ingredient component can be combined with an oral, non-toxic and pharmaceutically acceptable inert excipient. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules may be produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compound according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Pharmaceutical compositions adapted for oral administration can also be formulated by spray drying of a solid or liquid dispersion.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The thienopyridone derivative used according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

By "effective amount" it is meant the quantity of the compound as defined above which prevents, removes or reduces the deleterious effects of the treated disease in humans. It is understood that the administered dose may be adapted by those skilled in the art according to the patient, the pathology, the mode of administration, etc. For instance, the thienopyridone derivative may be administered once or twice a day at a daily dose of 0.5 mg to 300 mg for a human patient, preferably from 20 mg to 1000 mg, more preferably from 60 mg to 500 mg. It can be administered 4, 5, 6 or 7 days a week as a long-life medication.

In a particular embodiment of this invention, the thienopyridone derivative is administered as dosage units which comprise from 0.5 mg to 1500 mg, preferably from 20 mg to 1000 mg, more preferably from 60 mg to 500 mg of the thienopyridone derivative.

The invention will also be described in further detail in the following examples, which are not intended to limit the scope of this invention, as defined by the attached claims.

EXAMPLES

Example 1: Synthesis of PXL770

Analytical Methods
XRPD
X-Ray Powder Diffraction (XRPD) analyses were performed using a Panalytical Xpert Pro diffractometer equipped with a Cu (K alpha radiation) X-ray tube and a Pixcel detector system. The samples were analysed in transmission mode and held between low density polyethylene films. XRPD patterns were sorted, manipulated and indexed using HighScore Plus 2.2c software.
TG/DTA
Thermogravimetric (TG) analyses were carried out on a Perkin Elmer Diamond Thermogravimetric/Differential Temperature Analyser (TG/DTA). The calibration standards were indium and tin. Samples were placed in an aluminium sample pan, inserted into the TG furnace and accurately weighed. The samples were heated from 30-300° C. in a stream of nitrogen at a rate of 10° C./minute. The temperature of the furnace was equilibrated at 30° C. prior to the analysis of the samples.

1a) Synthesis of 1-(5-benzyloxytetralin-6-yl)ethanone (1)

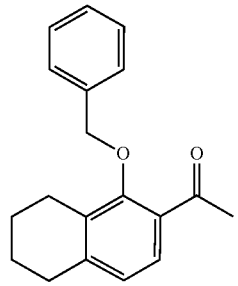

6-Acetyl-5-hydroxytetralin (100 g, 1 eq.) was dissolved in acetonitrile (300 mL). After addition of $K_2CO_3$ (1.1 eq.) and benzyl bromide (1.05 eq.), the suspension was heated (76° C.). After 48 hours, benzyl bromide (0.1 eq) was added. After overall 74 hours, the solid was filtered off and washed with acetonitrile (200 mL), and the combined filtrates were evaporated. Compound 1 was obtained as a syrup: m=148.6 g, quantitative yield, 96.6% a/a purity.

1b) Synthesis of ethyl 2-amino-4-(5-benzyloxytetralin-6-yl)thiophene-3-carboxylate (2)

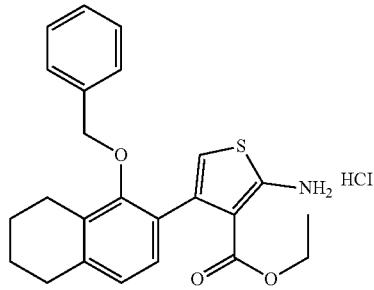

Acetic acid (70 mL) was heated to T=65° C. HMDS (1.5 eq.) was added over 10 min. Afterwards, a solution of compound 1 (69.5 g, 1 eq.) and ethyl cyanoacetate (1.5 eq.) in acetic acid (140 mL) was added. The resulting mixture was stirred at T=65° C. for 24 h.

After cooling to room temperature, aqueous NaOH (1 M, 140 mL) and TBME (210 mL) were added. The layers were separated. The organic layer was washed with aqueous NaOH (1 M, 4×140 mL) until the pH of the aqueous phase was basic (pH=13). The organic layer was washed with aqueous HCl (1M, 140 mL) and $H_2O$ (2×140 mL).

EtOH (240 mL), $NaHCO_3$ (1.3 eq.) and sulfur (1.0 atom eq.) were added. After heating to reflux for 180 min, the reaction mixture was concentrated to 210 mL and co-evaporated with TBME (3×140 mL). After cooling to room temperature, the suspension was filtered and the solid was washed with TBME (70 mL). The combined filtrates were concentrated to 210 mL and HCl in dioxane (1.1 eq.) was added dropwise at room temperature. After seeding, precipitation was observed. Heptane (350 mL) was added dropwise at room temperature. After stirring for 14 h, the suspension was filtered. After washing with heptane (3×70 mL) and drying, compound 2 was recovered as a solid. m=83.2 g, 71% yield, 93.7% a/a purity.

1c) Synthesis of ethyl 4-(5-benzyloxytetralin-6-yl)-5-chloro-2-[(2-phenylacetyl)amino]thiophene-3-carboxylate (3)

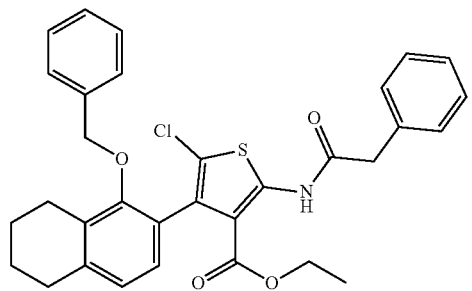

(3)

Compound 2 (17.69 g, 1 eq.) was dissolved in dichloromethane (140 mL). The resulting solution was cooled with ice/water. Under stirring, N-chlorosuccinimide (1.05 eq.) was added. The mixture became dark over a few minutes. After 1 h, phenylacetyl chloride (1.25 eq.) was added.

After 1 hour at 0° C. and 2 hours at room temperature, the mixture was evaporated down to ca. 35 mL and EtOH (2×70 mL) was added, and evaporated down again. The mixture was diluted with EtOH (35 mL) and cooled with ice/water. The product precipitated. The solid was filtrated and washed with cold EtOH (3×18 mL).

Compound 3 was obtained as a solid: m=20.99 g, 94.2% yield, 99.3% a/a purity.

1d) Synthesis of 3-(5-benzyloxytetralin-6-yl)-2-chloro-4-hydroxy-5-phenyl-7H-thieno[2,3-b]pyridin-6-one (4)

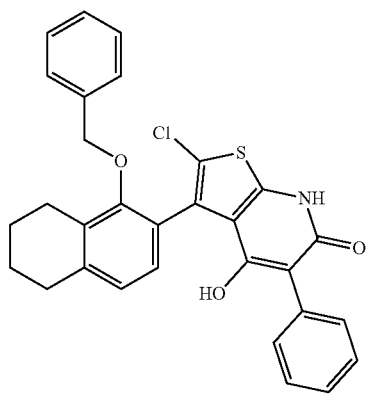

(4)

Compound 3 (19.88 g, 1 eq.) was solubilized in methyltetrahydrofuran (120 mL), and the reaction mixture was cooled to a temperature between −16° C. and −10° C. (NaCl/Ice). Potassium tert-butoxide (5 eq.) was added in four portions. Then, the reaction mixture was warmed up to room temperature, and stirred for 65 min at room temperature. A dropwise addition of 2N HCl (5 eq.) was carried out at T=0-5° C. (water/ice) and the resulting mixture was stirred vigorously. The organic phase was washed with $NaCl_{(aq)}$ (11%, 1×50 mL) and water (2×50 mL). The organic phase was concentrated to ~50% solution. Methyltetrahydrofuran (80 mL) was added, and the resulting solution was concentrated to ~50% solution. TBME (100 mL) was added, and the resulting solution was concentrated to ~50% solution (this step was repeated 3 times). Then, TBME (25 mL), seeds of compound 4 and n-Heptane (20 mL) were added and the resulting solution was stirred at room temperature overnight. The mixture was concentrated to ca. 50 mL, filtrated, rinsed with mother liquor and washed with n-Heptane (2×40 mL) and dried. Compound 4 was obtained as a granular solid. Yield 88%, 99.5% a/a purity.

1e) Synthesis of 2-chloro-4-hydroxy-3-(5-hydroxytetralin-6-yl)-5-phenyl-7H-thieno[2,3-b]pyridin-6-one (1)

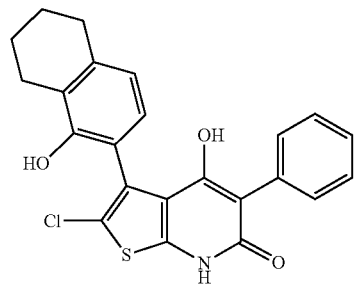

(I)

Compound 4 (15 g, 1 eq.) was dissolved in 75 mL of dichloromethane and was cooled to T=−10° C./−15° C. (with ice/NaCl). $BCl_3$ (1.5 eq., solution: 1 mol/L in dichloromethane) was added dropwise and the resulting mixture was stirred at room temperature for 15 hours. The resulting mixture was cooled with ice/water, and water (75 mL) was added. The resulting mixture was stirred vigorously and the organic phase was extracted with water/MeOH (9:1 v/v, 5×45 mL). The organic phase was concentrated, a solvent swap was carried out with toluene (3×90 mL) and diluted with toluene to reach a final volume of 90 mL of toluene. The resulting mixture was heated to reflux and 15 mL of methanol was added. A brownish solution with few particles was obtained. Seeds were added at T=40° C., warmed to T=52° C. and cooled to room temperature. The resulting mixture was stirred overnight, and then was cooled with ice/NaCl (T=−10° C./−15° C.) for 100 minutes. The precipitated product was filtrated, washed with toluene/heptane 1:2 v/v (15 mL) and heptane (15 mL) and dried. Crystals of compound (I) were obtained: 87% yield, 99.0% a/a purity.

1f) Synthesis of the monohydrate potassium salt of 2-chloro-4-hydroxy-3-(5-hydroxytetralin-6-yl)-5-phenyl-7H-thieno[2,3-b]pyridin-6-one (Ia)

Compound (I) was suspended in water/isopropanol mix (1/1, 5 parts of each solvents) then 0.50 to 0.55 eq of potassium carbonate was added. The pH was about 12 (pH indicator paper) at the end of the addition of potassium carbonate. After 3 hours of stirring at 50° C., the suspension was thicker and the pH was about 8 (pH indicator paper). The temperature was raised to 80° C. until a solution was obtained (10-15 minutes). A clarification can be done at this point of the process if required. 7 parts of water were added and the reaction mixture was then cooled to 40° C. (turbid solution observed). The solvent was distilled under reduce pressure (from 180 mbar to 40 mbar) at 40° C. until 7 parts of solvents remained in the reactor. Crystallization of potassium salt monohydrate may occur here. 4.2 parts of water were added and the mixture was seeded with compound (I) (1 to 2% of seeds). The suspension was then cooled down from 40° C. to 5° C. in 7 hours (5° C./hour) and kept at 5° C. for several hours. The suspension was filtered. The cake was washed twice by 1.42 parts of water. The collected solid was dried at 40° C. under vacuum given minimum 80% yield of Compound (Ia), at required chemical purity (i.e. 98%+).

Example 2: Characterization of PXL770 a) X-ray powder diffraction (XRPD) data of compound (Ia) indicated that it was composed of a crystalline material. The XRPD description of compound (Ia) is shown in Table 1.

TABLE 1

| Peak No | 2-theta (°) | d-value (Å) | Relative intensity (%) |
|---|---|---|---|
| 1 | 4.910 | 17.9826 | 15 |
| 2 | 11.560 | 7.6486 | 8 |
| 3 | 13.010 | 6.7992 | 25 |
| 4 | 14.720 | 6.0130 | 100 |
| 5 | 16.450 | 5.3843 | 11 |
| 6 | 17.330 | 5.1128 | 49 |
| 7 | 17.770 | 4.9872 | 14 |
| 8 | 18.690 | 4.7437 | 12 |
| 9 | 19.220 | 4.6141 | 16 |
| 10 | 19.640 | 4.5164 | 20 |
| 11 | 20.190 | 4.3946 | 8 |
| 12 | 21.170 | 4.1933 | 23 |
| 13 | 21.580 | 4.1145 | 12 |
| 14 | 22.190 | 4.0028 | 12 |
| 15 | 22.700 | 3.9140 | 26 |
| 16 | 23.240 | 3.8243 | 17 |
| 17 | 23.860 | 3.7263 | 23 |
| 18 | 24.410 | 3.6435 | 43 |
| 19 | 25.330 | 3.5133 | 10 |
| 20 | 26.230 | 3.3947 | 17 |
| 21 | 26.730 | 3.3323 | 23 |
| 22 | 28.700 | 3.1079 | 25 |
| 23 | 29.590 | 3.0164 | 11 |
| 24 | 29.950 | 2.9810 | 13 |
| 25 | 30.960 | 2.8860 | 36 |
| 26 | 31.570 | 2.8316 | 15 |
| 27 | 32.200 | 2.7776 | 18 |
| 28 | 33.080 | 2.7057 | 14 |
| 29 | 33.530 | 2.6704 | 17 |
| 30 | 34.050 | 2.6308 | 10 |
| 31 | 34.750 | 2.5794 | 26 |
| 32 | 35.530 | 2.5246 | 56 |
| 33 | 35.950 | 2.4960 | 22 |
| 34 | 36.660 | 2.4493 | 20 |
| 35 | 37.300 | 2.4087 | 11 |
| 36 | 38.320 | 2.3469 | 16 |
| 37 | 39.490 | 2.2801 | 13 | b) TG/DTA analysis showed an initial weight loss of 1.1% from 30-100° C., followed by larger weight loss of 3% from 117-160° C. due to loss of bound water. The second weight loss was accompanied by a large endotherm and the combined weight losses of 4% approximate the theoretical weight loss for a monohydrate (3.75% w/w). The compound decomposed above 240° C.

Example 3: In Vitro Experiments

Method:

pIMDCK cells were cultured at 37° C., 21% 02 und 5% $CO_2$ in a modified MEM-medium, containing "Earl's balanced salt solution", 2 mM L-Glutamine, 10% heat-shock inactivated FCS, 50 IU/ml penicillin and 50 µg/ml streptomycin. For cyst formation, pIMDCK cells were trypsinated and dissolved within a type I collagen suspension before being transferred into 24-well plates. 4 wells per condition and individual experiment were used. Next, cell culture medium was added, containing either 10 µM forskolin (control; Ctrl) or 10 µM forskolin+metformin or 10 µM forskolin+PXL770 in the given concentrations. The experiments were performed for 5 days. Thereafter, photos were taken in 4 different areas of each well (at 0, 3, 6 and 9 o'clock) using a Zeiss Primo Vert microscope with a Zeiss Axiocam 105 color camera (both Zeiss Microscopy GmbH, Jena, Deutschland). Then, diameters of the cysts were measured with ImageJ (V.1.48) in a blinded fashion. By assuming a spherical shape of the cysts, volumes were calculated by the use of the formula $4/3\pi r^3$. The average of all cysts of each condition and experiment was calculated. Control cyst volume was set to 100%. The results are shown on FIG. 1.

Figure 2:
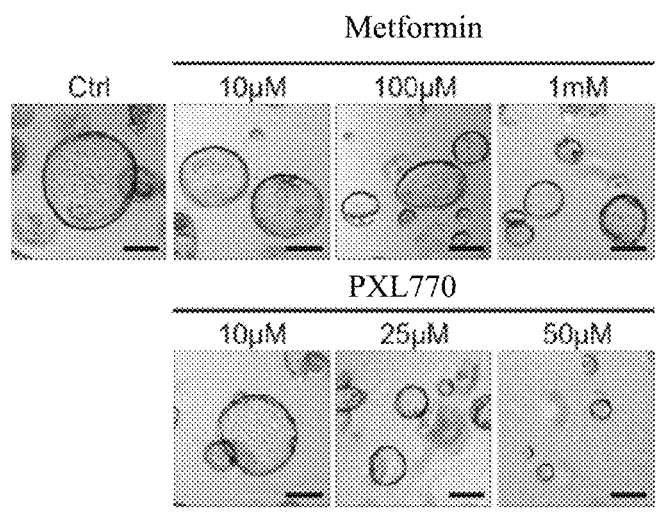
FIG. 2 shows photographs of the cysts formed from pIMDCK cells in the presence of 10 µM, 100 µM and 1 mM metformin or of 10 µM, 25 µM or 50 µM PXL770.

Photographs of the cysts were also taken and are shown on FIG. 2 (Scale Bars: 100 µm).

Results:

As shown on FIGS. 1 and 2, PXL770 significantly inhibits cyst growth, with lower doses than metformin.

Example 4: Comparative Experiments

In this example, various thienopyridone compounds were compared in an in vitro experiment, namely:

PXL770: potassium 2-chloro-3-(5-hydroxytetralin-6-yl)-6-oxo-5-phenyl-7H-thieno[2,3-b]pyridin-4-olate.

PXL700: 2-chloro-4-hydroxy-3-indan-5-yl-5-(3-pyridyl)-7H-thieno[2,3-b]pyridin-6-one PXL702: 2-chloro-4-hydroxy-3-(4hydroxyindan-5-yl)-5-phenyl-7H-thieno[2,3-b]pyridin-6-one PXL695: 2-chloro-5-(3-fluorophenyl)-4-hydroxy-3(4-hydroxyindan-5-yl)-7H-thieno[2,3-b]pyridin-6-one,

PXL037:

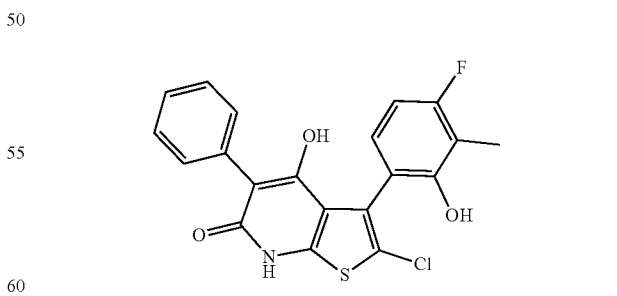

To investigate the effects of these compounds, an in vitro 3D cyst swelling assay using polycystic kidney disease (PKD) patient-derived primary cells embedded in a 3D culture matrix (referred to as the huPKD model) was used. Swelling of cysts can be visualised and quantified by high content microscopy.

Method

The 3D huPKD cyst swelling assay has been performed with huPKD05 cells.

3D culture and compound exposure. huPKD05 cells (PKD1 mutation: c.5622G>A p.Trp1874*) were mixed with PrimCyst-Gel (OcellO BV). 15 µL of cell-gel mix was pipetted to 384-well plates (Greiner µClear, Greiner Bio-One B.V.) using a CyBio Felix 96/250 robotic liquid dispenser (Analyik Jena AG). Gel-cell mix was plated at a final cell density of 450 cysts per well. After gel polymerization at 37° C. for 30 minutes, 33 µL culture medium (no serum included) was added to each well. Cells were grown in gel for 24 hours, after which the cells were co-exposed for 48 hours with desmopressin (ddAVP) (Tocris), which stimulate the cyst swelling, and with the following molecules PXL770, PXL037, PXL700, PXL695, PXL702.

TABLE 1 overview of exposure conditions

| | Treatment | Concentration | Stimulant | Concentration |
|---|---|---|---|---|
| Pos_ddAVP | DMSO | 0.1% | ddAVP | 2.5 µM |
| Neg | DMSO | 0.1% | DMSO | 0.1% |
| ddAVP | PXL770 or PXL037/PXL37 or PXL695 or PXL700 or PXL702 | 10, 5, 2.5, 0.5 µM | ddAVP | 2.5 µM |

Sample processing: After 48 hours, cultures were fixed with 4% Formaldehyde (Sigma Aldrich) and simultaneously permeabilized with 0.2% Triton-X100 (Sigma Aldrich) and stained with 0.25 µM rhodamine-phalloidin (Sigma Aldrich) and 0.1% Hoechst 33258 (Sigma Aldrich) in 1×PBS (Sigma Aldrich) for 2 days at 4° C., protected from light. After fixation and staining, plates were washed with 1×PBS, sealed with a Greiner SilverSeal (Greiner Bio-One B.V.) and stored at 4° C. prior to imaging.

Imaging and image analysis: Imaging was done using Molecular Devices ImageXpress Micro XLS (Molecular Devices) with a 4× NIKON objective. For each well around 35 images in the Z-direction were made for both channels, capturing the whole z-plane in each image. Image analysis was performed using Ominer™ software (OcellO BV). Cysts were segmented using detection of Hoechst-stained nuclei and Rhodamine-phalloidin-stained cellular f-actin. Cyst area was determined by calculating for the area in pixels (px) of each object in every in-focus plain. This was averaged per well and normalized between solvent control (0%) and stimulant only (100%). Statistics was done using GraphPad Prism, graphs were prepared in GraphPad Prism 6 (GraphPad Software, La Jolla, Calif.).

Results

Figure 3:
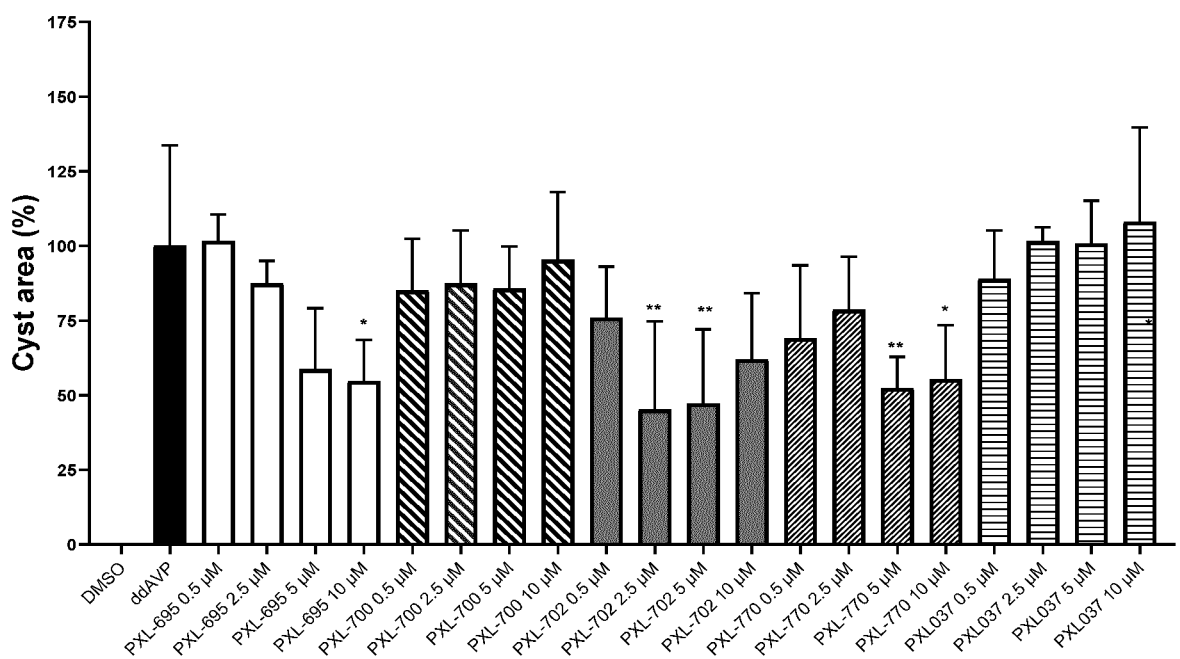
FIG. 3 shows the results of an in vitro experiment assessing the efficacy on cyst swelling of various thienopyridones of this invention compared to similar compounds.

The results of the above experiments are shown on FIG. 3.

Control conditions: A significant assay window was established between Desmopressin (ddAVP) stimulated and unstimulated (solvent control, DMSO) (FIG. 1) (ddAVP only vs. DMSO, p<0.0001).

PXL770, PXL695, PXL700, PXL702 and PXL037:

PXL770 PXL695, PXL700, PXL702 and PXL037 were tested at 4 concentrations: 10, 5, 2.5, 0.5 µM in the presence of ddAVP. (2.5 µM).

PXL770 dose-dependently reduced cyst area and this effect was significant at 5 and 10 µM compared to ddAVP alone reaching 50% reduction for both PXL770 5 and 10 µM (p<0.01 and p<0.05 respectively vs. ddAVP alone). While not shown on FIG. 3, it should be noted that PXL770 offered 75% reduction of cyst area at 25 µM (p<0.0001 vs. ddAVP alone).

PXL695 and PXL702 dose-dependently reduced cyst area.

In contrast, PXL037 and PXL700 exhibited no significant effect compared to ddAVP alone.

CONCLUSION

PXL770, PXL037, PXL770, PXL695 and PXL702 were assessed in huPKD cyst swelling assay to investigate their potency in inhibiting desmopressin (ddAVP) induced cyst swelling.

PXL770 dose dependently reduced cyst swelling. PXL770 at 5 and 10 µM inhibited almost 50% of the induced swelling.

Similar potency and efficacy were achieved with PXL695 and PXL702.

PXL037 and PXL700 had no effect on cyst area up to 10 µM.

The invention claimed is:

1. A method of limiting renal cyst growth or reducing renal cyst volume in a subject having autosomal dominant polycystic kidney disease (ADPKD) comprising administering to the subject having ADPKD a compound of formula (II)

(II)

or a pharmaceutically acceptable salt and/or solvate thereof in an amount that limits renal cyst growth or reduces renal cyst volume.

2. The method according to claim 1, wherein said compound is administered once or twice a day at a daily dose of a) 0.5 mg to 3000 mg, b) 20 mg to 1000 mg, or c) 60 mg to 500 mg.

3. The method according to claim 1, wherein the compound is a monohydrate potassium salt of formula (Ia):

(Ia)

4. The method according to claim 1, wherein a salt and/or a hydrate of the compound of formula (II) is administered to the subject.

5. The method according to claim 1, wherein the compound of formula (II) or a pharmaceutically acceptable salt and/or solvate thereof is administered orally.

6. The method according to claim 1, wherein the compound of formula (II) or a pharmaceutically acceptable salt and/or solvate thereof, is orally administered at a daily dose from 20 mg to 1000 mg to the subject.

* * * * *